United States Patent [19]

Metz

[11] Patent Number: 5,001,268
[45] Date of Patent: Mar. 19, 1991

[54] PREPARATION OF N-ARYLSUBSTITUTED AMIDES
[75] Inventor: Francois Metz, Lyon, France
[73] Assignee: Rhone-Poulenc Chimie, Courbevoie, France
[21] Appl. No.: 527,268
[22] Filed: May 23, 1990
[51] Int. Cl.$^5$ .................. C07C 231/00; C07C 231/02; C07C 231/10
[52] U.S. Cl. .................................................... 564/132
[58] Field of Search .......................................... 564/132
[56]       References Cited
           U.S. PATENT DOCUMENTS
    4,866,177  9/1989  Lin ................................... 564/132 X Primary Examiner—Richard L. Raymond
Attorney, Agent, or Firm—Burns, Doane, Swecker & Mathis

[57] ABSTRACT

The N-arylsubstituted amides, e.g., N-phenylformamide and acetanilide, are prepared by reacting at least one nitroaromatic compound with carbon monoxide and at least one carboxylic acid, in liquid phase and under superatmospheric pressure, in the presence of a catalytically effective amount of palladium or a palladium compound and at least one heterocyclic compound having the formula:

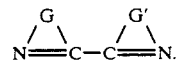

13 Claims, No Drawings

PREPARATION OF N-ARYLSUBSTITUTED AMIDES

BACKGROUND OF THE INVENTION

1. Field of the Invention

The present invention relates to the preparation of N-arylsubstituted amides, and, more especially, to the preparation of such amides via reductive N-acylation of nitroaromatic compounds by means of carboxylic acids and carbon monoxide.

2. Description of the Prior Art

The N-substituted amides are known to this art to be particularly useful intermediates for the synthesis of a wide variety of pharmaceuticals and agrochemicals.

It too has been proposed to this art to prepare N-arylsubstituted amides by the reductive acylation of nitroaromatic compounds.

Thus, *Bulletin of the Chemical Society of Japan*, Vol. 42, 827–828 (1969) describes the conversion of nitrobenzene into acetanilide or propionanilide, respectively, by reacting it with carbon monoxide and acetic or propionic acid, at a temperature greater than 300° C., under initial carbon monoxide pressures, measured at ambient temperature, ranging from 50 to 100 kg/cm$^2$, and in the presence of nickel tetracarbonyl, dicobalt octacarbonyl or iron pentacarbonyl. Nonetheless, the application of such a process on an industrial scale is largely compromised by the excessively severe operating conditions (temperature and pressure) required.

More recently, an alternative to the above catalyst system has been described in *J. Org. Chem.*, 49, 4451–4455 (1984); it comprises a platinum complex, such as PtCl$_2$(PPh$_3$)$_2$ and tin (IV) chloride or another Lewis acid, such as SnCl$_2$, FeCl$_3$, VCl$_3$, AlCl$_3$ or ZnCl$_2$. If the presence of such Lewis acids is indispensable in order to obtain an appropriate acetanilide selectivity, a temperature of at least 180° C. is required to achieve an appreciable conversion of the nitrogen compounds. Furthermore, this conversion is accompanied most frequently by the undesirable co-production of aniline. The required presence of rare and expensive platinum complexes also militates against application of such process on an industrial scale, even though its basic principle is quite valid.

Thus, serious need continues to exist for alternate catalyst systems to those heretofore proposed to this art.

SUMMARY OF THE INVENTION

Accordingly, a major object of the present invention is the provision of an improved process for the preparation of N-arylsubstituted amides by reacting at least one nitroaromatic compound with carbon monoxide and at least one carboxylic acid under conditions of temperature and pressure that are conspicuously less severe than those to date characterizing the state of this art, while at the same time limiting the co-production of any aromatic amine, which improved process is carried out in the presence of a catalyst system based on palladium or a palladium compound and at least one particular heterocyclic compound additive.

Briefly, the present invention features a process for the preparation of N-arylsubstituted amides, comprising reacting, in liquid phase and at a pressure higher than atmospheric, at least one nitroaromatic compound with carbon monoxide and at least one carboxylic acid, in the presence of a catalytically effective amount of palladium or a palladium compound and at least one heterocyclic compound additive of the formula:

wherein G and G', which may be identical or different, are each a divalent bridging radical having 3 or 4 atoms, at least 2 of which are carbon atoms, with the proviso that G and G' may be joined together.

DETAILED DESCRIPTION OF THE PREFERRED EMBODIMENTS OF THE INVENTION

More particularly according to the present invention, in a preferred embodiment thereof, the N-aryl-substituted formamides are prepared by reacting at least one nitroaromatic compound with carbon monoxide and formic acid in the presence of the above co-catalyst system.

In another preferred embodiment of the invention, p-acetylaminophenol is prepared by reacting carbon monoxide and acetic acid with p-nitrophenol in the presence of such co-catalyst system.

The process according to the present invention may be represented schematically by the following stoichiometric equation:

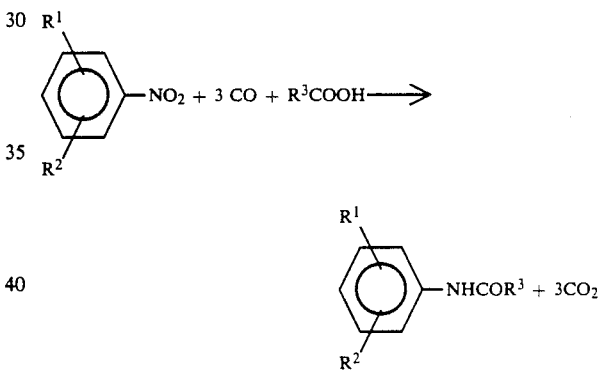

wherein R$^1$ and R$^2$, which may be identical or different, are each a hydrogen atom, a hydroxyl group (—OH), a nitro group (—NO$_2$), a halogen atom, a linear or branched chain alkyl radical having up to 12 carbon atoms or a halo-substituted such radical, or an alkoxy radical having up to 4 carbon atoms; and R$^3$ is a hydrogen atom, or a linear or branched chain alkyl radical having up to 12 carbon atoms or a halo-substituted such radical, with the proviso that R$^1$, R$^2$ and R$^3$ may be identical or different.

Advantageously, R$^1$ and R$^2$, which may be identical or different, are each a hydrogen atom, a hydroxyl group, a nitro group, or a linear or branched chain alkyl radical having up to 4 carbon atoms or a fluorine, chlorine and/or bromine-substituted such radical (the hydrogen atoms of which either being partially or completely replaced by such halogen atoms), and, preferably, if one is a hydroxyl or nitro group, the other is hydrogen or an alkyl radical having up to 4 carbon atoms.

Exemplary of the nitroaromatic compound starting materials suitable for use in the present invention, the following are representative:

Nitrobenzene;

p-Nitrotoluene;
o-Nitrotoluene;
2,4-Dinitrotoluene;
p-Nitroanisole;
p-Nitrophenol;
p-Nitrochlorobenzene; and
p-(Trifluoromethyl)nitrobenzene.

The subject process requires at least one carboxylic acid starting material of the formula $R^3COOH$, in which $R^3$ is as defined above.

Advantageously, $R^3$ is a hydrogen atom or an alkyl radical having up to 4 carbon atoms.

Exemplary such carboxylic acids include formic acid, acetic acid and propionic acid.

The stoichiometric equation given above indicates equimolar amounts of the nitroaromatic compound and carboxylic acid. The amount of the carboxylic acid to be used may vary widely from this 1/1 (molar) proportion and the precise amount of the acid to be introduced is typically larger than this proportion. The excess carboxylic acid that is desirable to use in the reaction will depend greatly on the precise nature of the carboxylic acid employed and on various other parameters of the process which affect the favorable progress thereof.

Thus, for example, if formic acid is used, good results may be obtained using a molar carboxylic acid/nitroaromatic compound ratio ranging from 1 to 10 and preferably from approximately 2 to 4.

To the contrary, if, for example, acetic acid is used, good results may be obtained using a molar ratio greatly in excess of 10.

The process according to the present invention requires the presence of a catalytically effective amount of palladium or a palladium compound.

Any source of palladium is suitable for this purpose. Indeed, metallic palladium may be used as is, or deposited onto an inert support such as carbon black or alumina, or as a palladium salt or complex thereof.

Under the conditions of this reaction, the majority of these palladium sources will be soluble in the reaction medium. Exemplary palladium compounds suitable for use in the process of the invention, the following are representative:

(i) palladium carboxylates, the anion of which preferably contains a maximum of 12 carbon atoms and in particular palladium acetate and palladium propionate;

(ii) palladium halides and in particular palladium chloride and palladium bromide;

(iii) palladium acetylacetonate, complexes of palladium and dibenzylideneacetone (dba), such as $Pd(dba)_3$.

Palladium acetate is especially suitable for use in the process according to the invention.

The precise amount of palladium to be used may vary over wide limits and generally is established as a result of a compromise between the desired efficiency, cost of the catalyst, and the other conditions selected for the reaction.

A molar ratio of the groups $NO_2/Pd$ ranging from 1,000 to 200 appears to be generally satisfactory; a ratio higher than 1,000 may limit the velocity of the reaction and a ratio of less than 200 adversely affects the overall economy of the process.

The process of this invention also requires at least one heterocyclic additive of the following formula, in which G and G' are as defined above:

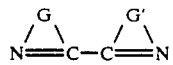

If the bridge radical or radicals G and/or G' contain one (or two) atoms other than carbon atoms, these atoms preferably are nitrogen atoms. G and G' may be joined together by a group of two carbon atoms to constitute an additive of the above formula, representing the skeleton of 1,10-phenanthroline.

Exemplary additives of the above general formula are 2,2'-bipyridyl, 4,4'-dimethyl-2,2'-bipyridyl, 4,4'-dimethoxy-2,2'-bipyridyl, 4,4'-dicarboxy-2,2-bipyridyl, 4,4'-dichloro-2,2'-bipyridyl, 2,2'-biquinolyl, 1,10-phenanthroline, 4,7-diphenyl-1,10-phenanthroline, 3,4,7,8-tetramethyl-1,10-phenanthroline and 4,7-dimethyl-1,10-phenanthroline. 1,10-Phenanthroline and derivatives thereof, unsubstituted in the 2- and/or the 9-position, are particularly advantageous additives for the process of this invention.

The amount of the additive may vary over wide limits. It is generally such that the molar ratio of additive/Pd ranges from 1 to 100 and preferably ranges from 4 to 20.

The reaction temperature, in particular, depends on the reactivity of the nitroaromatic compound. A temperature of at least 110° C. appears to be necessary to obtain acceptable conversion and there is no advantage in operating above 180° C., at which an appreciable decrease in the selectivity for the desired amide is observed. Preferably, the temperature ranges from 120° to 160° C.

The reaction is carried out in the liquid phase under a pressure higher than atmospheric. A partial pressure of carbon monoxide at temperature on the order of 30 bar (3,000 KPa) is well suited for the satisfactory progress of the reaction. It is not advantageous to exceed 150 bar (15,000 KPa).

The pressure advantageously ranges from 30 to 120 bar (3,000 to 12,000 KPa). Essentially pure carbon monoxide is used, such as is commercially available, with minor amounts of inert gases, such as nitrogen, argon and carbon dioxide, being perfectly tolerable. The presence of hydrogen, even in appreciable amounts, does not adversely affect the reaction, but it is capable of effecting an appreciable, even if slight, reduction in selectivity for the desired compounds.

It will of course be appreciated that the subject reaction may be carried out in the presence of a solvent or diluent that is inert relative to the reaction and the reaction products. Exemplary such solvents or diluents include the aromatic hydrocarbons, whether or not chlorinated, benzene and o-dichlorobenzene, aliphatic or cyclic ethers, N,N-substituted amides, sulfones and esters.

Certain carboxylic acids (reagents) such as, in particular, acetic acid, may be used in a large excess relative to the stoichiometric amount and thus may also serve as a supplementary solvent or diluent.

Following the predetermined duration of the reaction, the desired amide is separated from the reaction medium by any appropriate means, for example by extraction and/or distillation.

In order to further illustrate the present invention and the advantages thereof, the following specific examples are given, it being understood that same are intended only as illustrative and in nowise limitative.

EXAMPLES 1 to 8

Preparation of N-phenylformamide

Operating procedure

The operating procedure is described with reference to Example 2:

Into a 125 ml, Hastelloy B 2 autoclave, 36 mmole of nitrobenzene ($\phi NO_2$), 0.36 matg palladium in the form of Pd(OAc)$_2$, 3 mmoles of 1,10-phenanthroline (phen.), 72 mmole formic acid and o-dichlorobenzene qsp 30 ml (odcb) were introduced.

The autoclave was purged with carbon monoxide, then heated under agitation at 140° C., under 60 bar (6,000 KPa) of CO, at constant pressure. After 1 hour of reaction at the temperature indicated, the autoclave was cooled and degassed. The reaction mass was withdrawn, diluted with ethanol (qsp 100 ml) and analyzed by gas phase chromatography.

Examples 1 and 3 to 8 were similarly carried out.

The particular conditions and the results obtained are reported in Table I, in which the initial charges were relative to 1 mole of nitrobenzene and the following conventions are used:

| | |
|---|---|
| T | reaction temperature in °C.; |
| t | reaction duration in hours (h); |
| P | CO pressure, in temperature and bar; |
| TT % | degree of nitrobenzene converted; |
| RT % (NPF) | number of moles of N-phenylformamide formed per 100 moles of nitrobenzene converted; |
| RT % (A) | number of moles of aniline formed per 100 moles of nitrobenzene converted. |

EXAMPLE 9

The procedure of Example 2 was repeated, but replacing the 1,10-phenanthroline by an equivalent amount of 2,2'-bipyridyl.

The results obtained were as follows:

| | |
|---|---|
| TT % | 59 |
| RT % (NPF) | 79 |
| RT % (A) | 2 |

EXAMPLES 10 to 12

Preparation of different N-arylformamides (NAF)

In the apparatus described above and repeating the above procedure, a series of experiments was carried out at 140° C. under 60 bar, beginning with three distinct nitroaromatic compounds.

Example 10 was carried out using o-nitrotoluene, Example 11 using 2,4-dinitrotoluene and Example 12 using 4-trifluoromethylnitrobenzene.

Upon completion of each experiment, the reaction mass extracted was withdrawn, then evaporated and distilled. The distillate was analyzed by gaseous phase chromatography, by combined CPG/mass spectroscopy and NMR.

The specific conditions and the results obtained are reported in Table II, in which the initial charges are reduced to 1 mole of the nitroaromatic compound and in which:

| | |
|---|---|
| TT % | degree of conversion of the starting nitroaromatic compound; |
| RT % (NAF) | the number of moles of N-arylformamide formed per 100 moles of nitroaromatic compound converted. |

EXAMPLES 13 and 14

Preparation of acetanilide and p-acetylaminophenol

In the apparatus described and repeating the above procedure, two syntheses were successively carried out at 140° C. under 60 bar and in the absence of o-dichlorobenzene.

Analysis after the synthesis of acetanilide was carried out as indicated in Examples 1 to 8; the analysis corresponding to the synthesis of p-acetylaminophenol was carried out by CLHP on the reaction mass withdrawn and evaporated beforehand.

Specific conditions and the results obtained are reported in Table III.

TABLE I

| | Initial Charges mole | | | | ml | Operating conditions | | | | | |
|---|---|---|---|---|---|---|---|---|---|---|---|
| Example | $\phi NO_2$ | HCOOH | Pd | phen. | odcb | T° C. | t | P | TT % | RT % (NPF) | RT % (A) |
| 1 | 1 | 20 | 0.01 | 0.085 | — | 140 | 3 | 60 | 10 | 42 | 0 |
| 2 | 1 | 2 | 0.01 | 0.085 | 640 | 140 | 1 | 60 | 65 | 86 | 0 |
| 3 | 1 | 1.2 | 0.01 | 0.085 | 700 | 140 | 2 | 60 | 40 | 83 | 0.5 |
| 4 | 1 | 10 | 0.01 | 0.085 | 280 | 140 | 2 | 60 | 9 | 38 | 2 |
| 5 | 1 | 2 | 0.01 | 0.085 | 650 | 140 | 1 | 30 | 38 | 84 | 0 |
| 6 | 1 | 2 | 0.01 | 0.085 | 650 | 110 | 1 | 60 | 18 | 84 | 2 |
| 7 | 1 | 2 | 0.01 | 0.085 | 650 | 180 | 1 | 60 | 84 | 81 | 1 |
| 8 | 1 | 2 | 0.005 | 0.085 | 650 | 140 | 1 | 60 | 54 | 89 | 0 |

TABLE II

| | Nitroaromatic compound | | HCOOH | Pd | Phen. | odcb | | | |
|---|---|---|---|---|---|---|---|---|---|
| Example | Nature | mole | mol | atg | mol | ml | t | TT % | RT % (NAF) |
| 10 | 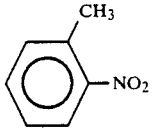 | 1 | 2 | 0.01 | 0.09 | 640 | 2 | 50 | 41 |

TABLE II-continued

| Example | Nitroaromatic compound Nature | mole | HCOOH mol | Pd atg | Phen. mol | odcb ml | t | TT % | RT % (NAF) |
|---|---|---|---|---|---|---|---|---|---|
| 11 | (2,4-dinitrotoluene) | 1 | 4 | 0.01 | 0.09 | 560 | 2 | 24 | N.B. |
| 12 | (4-nitro-trifluoromethylbenzene) | 1 | 2 | 0.01 | 0.09 | 640 | 1 | 100 | 78 |

N.B.: The formation of the following two formamides was observed:

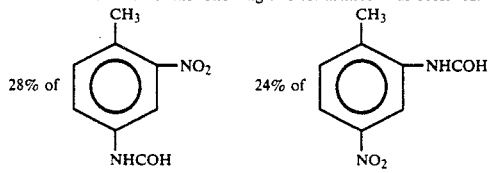

28% of [structure with CH₃, NO₂, NHCOH]   24% of [structure with CH₃, NHCOH, NO₂]

TABLE III

| Example | Nitroaromatic compound Nature | mole | H₃COOH mol | Pd atg | phen. mol | P | T °C. | t | TT (*) % | RT (**) % |
|---|---|---|---|---|---|---|---|---|---|---|
| 13 | nitrobenzene | 1 | 13 | 0.008 | 0.08 | 60 | 140 | 3.5 | 100 | 92 |
| 14 | p-nitrophenol | 1 | 13 | 0.008 | 0.08 | 60 | 140 | 3 | 98 | 61 |

(*) of the nitroaromatic compound
(**) respectively, in anilidine and p-acetylaminophenol While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of an N-arylsubstituted amide, comprising reacting at least one nitroaromatic compound with carbon monoxide and at least one carboxylic acid, in liquid phase and under superatmospheric pressure, in the presence of a catalytically effective amount of palladium or a palladium compound and at least one heterocyclic compound having the formula:

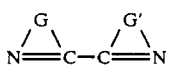

wherein G and G', which may be identical or different, are each an organic bridging radical having 3 or 4 atoms, at least two of which are carbon atoms, with the proviso that G and G' may be joined together.

2. The process as defined by claim 1, carried out at a temperature ranging from 110° to 180° C.

3. The process as defined by claim 1, wherein the partial pressure of the carbon monoxide is at least 30 bar (3,000 KPa).

4. The process as defined by claim 3, wherein the partial pressure of the carbon monoxide is no greater than 120 bar (12,000 Kpa).

5. The process as defined by claim 1, said at least one nitroaromatic compound comprising nitrobenzene, a nitrotoluene, p-(trifluoromethyl)nitrobenzene or p-nitrophenol.

6. The process as defined by claim 1, said at least one carboxylic acid comprising acetic acid.

7. The process as defined by claim 1, said at least one carboxylic acid comprising formic acid.

8. The process as defined by claim 5, said at least one nitroaromatic compound comprising p-nitrophenol.

9. The process as defined by claim 1, said at least one heterocyclic compound comprising 2,2'-bipyridyl, 4,4'-dimethyl-2,2'-bipyridyl, 4,4'-dimethoxy-2,2'-bipyridyl, 4,4'-dicarboxy-2,2-bipyridyl, 4,4'-dichloro-2,2'-bipyridyl, 2,2'-biquinolyl, 1,10-phenanthroline, 4,7-diphenyl-1,10phenanthroline, 3,4,7,8-tetramethyl-1,10-phenanthroline or 4,7-dimethyl-1,10-phenanthroline.

10. The process as defined by claim 9, said at least one heterocyclic compound comprising 1,10-phenanthroline or derivative thereof.

11. The process as defined by claim 1, wherein the group molar ratio NO₂/Pd ranges from 1,000 to 200.

12. The process as defined by claim 1, wherein the molar ratio heterocyclic compound/Pd ranges from 1 to 100.

13. The process as defined by claim 1, said at least one nitroaromatic compound having the formula:

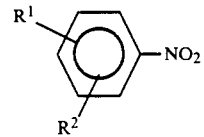

wherein $R^1$ and $R^2$, which may be identical or different, are each a hydrogen atom, a hydroxyl group, a nitro group, a halogen atom, a linear or branched chain alkyl radical having up to 12 carbon atoms or a halo-substituted such radical, or an alkoxy radical having up to 4 carbon atoms.

* * * * *